(12) United States Patent
Miller et al.

(10) Patent No.: US 10,463,273 B2
(45) Date of Patent: Nov. 5, 2019

(54) HYDRATION MONITOR

(71) Applicant: Halo Wearables LLC, Plymouth, MI (US)

(72) Inventors: Devin Warner Miller, Morgan, UT (US); David Rich Miller, Morgan, UT (US)

(73) Assignee: Halo Wearables, LLC, Morgan, UT (US)

(*) Notice: Subject to any disclaimer, the term of this patent is extended or adjusted under 35 U.S.C. 154(b) by 1179 days.

(21) Appl. No.: 13/756,742

(22) Filed: Feb. 1, 2013

(65) Prior Publication Data
US 2014/0221792 A1 Aug. 7, 2014

(51) Int. Cl.
A61B 5/00 (2006.01)
A61B 5/053 (2006.01)
A61B 5/01 (2006.01)
A61B 5/024 (2006.01)
A61B 5/11 (2006.01)
A61B 5/145 (2006.01)

(52) U.S. Cl.
CPC .......... A61B 5/0537 (2013.01); A61B 5/0075 (2013.01); A61B 5/01 (2013.01); A61B 5/024 (2013.01); A61B 5/1118 (2013.01); A61B 5/14546 (2013.01); A61B 5/6801 (2013.01)

(58) Field of Classification Search
USPC .................................................. 600/300–301
See application file for complete search history.

(56) References Cited

U.S. PATENT DOCUMENTS

| 5,389,097 | A  | * | 2/1995 | Bennett ............... | G01M 3/187 340/540 |
| 5,862,803 | A  | * | 1/1999 | Besson ............... | A61B 5/14552 128/903 |
| 6,370,426 | B1 | * | 4/2002 | Campbell ............ | A61B 5/0531 324/696 |
| 6,605,038 | B1 | * | 8/2003 | Teller .................... | A61B 5/411 128/904 |
| 6,850,162 | B2 | * | 2/2005 | Cacioli ................. | G01M 3/027 2/159 |
| 7,033,321 | B1 | * | 4/2006 | Sarvazyan ............ | A61B 5/411 600/449 |

(Continued)

Primary Examiner — Michael W Kahelin
Assistant Examiner — Shirley X Jian
(74) Attorney, Agent, or Firm — Miller IP Law, LLC

(57) ABSTRACT

A hydration monitoring apparatus is disclosed. The hydration monitoring apparatus comprises at least one sensor and an analysis unit. The hydration monitoring apparatus may take at least one biometric, biological, and/or physiological measurement of an individual and measures the hydration level, dehydration level or status, or bodily fluid level of an individual. The hydration monitoring apparatus indicates the hydration level, dehydration level or status, or bodily fluid level of an individual based on one or more biometric, biological, and/or physiological measurements. In one embodiment of the invention, the hydration monitoring apparatus determines whether to inform the user of their hydration level, dehydration level or status, or bodily fluid level. In one embodiment the hydration monitoring apparatus further comprises an informing device that informs the individual that the individual is approaching dehydration.

11 Claims, 5 Drawing Sheets

(56) References Cited

U.S. PATENT DOCUMENTS

| | | | | |
|---|---|---|---|---|
| 7,285,090 B2* | 10/2007 | Stivoric | A61B 5/01 | 128/905 |
| 7,539,533 B2* | 5/2009 | Tran | A61B 5/0022 | 600/509 |
| 7,558,622 B2* | 7/2009 | Tran | A61B 5/0022 | 600/509 |
| 7,689,437 B1* | 3/2010 | Teller | A61B 5/411 | 600/300 |
| 7,733,224 B2* | 6/2010 | Tran | G06F 19/3418 | 340/540 |
| 7,945,317 B2* | 5/2011 | Levin | A61B 5/0537 | 600/547 |
| 7,959,567 B2* | 6/2011 | Stivoric | A61B 5/411 | 128/921 |
| 8,103,333 B2* | 1/2012 | Tran | A61B 5/0022 | 600/509 |
| 8,249,686 B2* | 8/2012 | Libbus | A61B 5/0002 | 600/301 |
| 8,323,188 B2* | 12/2012 | Tran | A61B 5/0022 | 600/300 |
| 8,398,546 B2* | 3/2013 | Pacione | A61B 5/411 | 128/920 |
| 8,419,727 B2* | 4/2013 | Koss | A61B 18/1206 | 606/34 |
| 8,460,189 B2* | 6/2013 | Libbus | A61B 5/0006 | 600/301 |
| 8,684,900 B2* | 4/2014 | Tran | A61B 8/488 | 600/3 |
| 8,718,752 B2* | 5/2014 | Libbus | A61B 5/0006 | 600/515 |
| 8,823,490 B2* | 9/2014 | Libbus | A61B 5/0006 | 340/6.1 |
| 8,870,766 B2* | 10/2014 | Stivoric | A61B 5/01 | 600/301 |
| 8,961,413 B2* | 2/2015 | Teller | A61B 5/02055 | 600/301 |
| 8,961,414 B2* | 2/2015 | Teller | A61B 5/02055 | 600/301 |
| 8,965,498 B2* | 2/2015 | Katra | A61B 5/0537 | 600/547 |
| 9,028,405 B2* | 5/2015 | Tran | A61B 5/0022 | 600/300 |
| 9,033,875 B2* | 5/2015 | Teller | A61B 5/411 | 600/301 |
| 9,433,370 B2* | 9/2016 | Koyama | A61B 5/0537 | |
| 9,579,040 B2* | 2/2017 | Rafferty | A61B 5/6831 | |
| 2003/0120170 A1* | 6/2003 | Zhu | A61B 5/0537 | 600/547 |
| 2005/0070778 A1* | 3/2005 | Lackey | A61B 5/0537 | 600/366 |
| 2005/0192488 A1* | 9/2005 | Bryenton | A61B 5/02055 | 600/301 |
| 2006/0058593 A1* | 3/2006 | Drinan | A61B 5/0531 | 600/301 |
| 2006/0224053 A1* | 10/2006 | Black | A61B 5/0048 | 600/310 |
| 2006/0253007 A1* | 11/2006 | Cheng | A61B 5/0048 | 600/310 |
| 2007/0273504 A1* | 11/2007 | Tran | A61B 5/0022 | 340/539.12 |
| 2007/0276270 A1* | 11/2007 | Tran | A61B 5/0022 | 600/508 |
| 2008/0001735 A1* | 1/2008 | Tran | G06F 19/3418 | 340/539.22 |
| 2008/0039700 A1* | 2/2008 | Drinan | A61B 5/0537 | 600/301 |
| 2008/0146890 A1* | 6/2008 | LeBoeuf | A61B 5/0059 | 600/300 |
| 2009/0048497 A1* | 2/2009 | Keren | A61B 5/02028 | 600/301 |
| 2009/0227876 A1* | 9/2009 | Tran | A61B 5/0022 | 600/483 |
| 2010/0114204 A1* | 5/2010 | Burnes | A61N 1/37 | 607/4 |
| 2010/0234755 A1* | 9/2010 | Latman | A61B 5/05 | 600/547 |
| 2011/0301441 A1* | 12/2011 | Bandic | A61B 5/0059 | 600/306 |
| 2012/0095352 A1* | 4/2012 | Tran | A61B 5/0022 | 600/490 |
| 2013/0023781 A1* | 1/2013 | Freeman | A61B 5/0535 | 600/529 |
| 2013/0041235 A1* | 2/2013 | Rogers | A61B 5/6867 | 600/306 |
| 2013/0172691 A1* | 7/2013 | Tran | A61B 8/488 | 600/301 |
| 2013/0245388 A1* | 9/2013 | Rafferty | A61B 5/6831 | 600/301 |
| 2014/0018641 A1* | 1/2014 | Yoshino | A61B 5/01 | 600/301 |
| 2014/0035761 A1* | 2/2014 | Burton | G01D 4/002 | 340/870.02 |
| 2014/0143064 A1* | 5/2014 | Tran | A61B 5/0022 | 705/14.66 |
| 2014/0221792 A1* | 8/2014 | Miller | A61B 5/0537 | 600/309 |
| 2015/0094548 A1* | 4/2015 | Sabatini | A61B 5/0053 | 600/306 |
| 2015/0126845 A1* | 5/2015 | Jin | A61B 5/726 | 600/383 |
| 2015/0289820 A1* | 10/2015 | Miller | A61B 5/7221 | 600/300 |
| 2015/0305675 A1* | 10/2015 | Miller | A61B 5/0205 | 600/301 |
| 2016/0051191 A1* | 2/2016 | Miller | A61B 5/681 | 600/300 |
| 2016/0213303 A1* | 7/2016 | Hyde | A61B 5/1113 | |
| 2016/0213315 A1* | 7/2016 | Hyde | A61B 5/4875 | |
| 2016/0213316 A1* | 7/2016 | Hyde | A61B 5/4875 | |

\* cited by examiner

HYDRATION MONITOR

BACKGROUND

Dehydration is a condition in which water in a living body decreases below the individual's normal functioning level. Dehydration often occurs when an individual is exercising for extended periods of time, intakes little or no water, or the temperature rises to a point where an individual cannot excrete enough sweat to maintain their normal body temperature. Persons that regularly exert themselves in low humidity and/or high temperature conditions and/or for extended periods of time are prone to experience dehydration or dehydration symptoms. Elderly persons and children are also especially prone to experience dehydration or dehydration symptoms.

In less severe cases of dehydration, an individual's ability to perform tasks will begin to deteriorate. For example, in the case of long distance endurance athletes, an individual that becomes dehydrated by loss of as little as 2% body weight may begin to have their performance impaired. Losses in excess of 5% of body weight can decrease the capacity of an individual to perform a task by as much as 30%.

Another group of people in danger of dehydration are individuals with dysentery. Dysentery is a gastrointestinal disorder characterized by inflammation of the intestines, particularly the colon. Diarrhea and vomiting are typical side effects of patients with dysentery, especially in the case of small children. As dysentery patients suffer from diarrhea and vomiting they are unable to maintain a proper hydration level, causing them to become dehydrated. Such a dehydrated state exasperates the patient's condition, causing their health to further deteriorate and prolong recovery time.

If a dehydrated individual continues untreated, the effects of dehydration will progressively become worse until the individual is in a serious dehydrated condition. Typically when at least one third of the water in a living body is lost, the body temperature regulation ceases to function correctly. This dysfunction causes the body temperature to increase, which causes the water level in the living body to be further reduced and thus the body enters an uncontrolled spiral. As the body becomes more dehydrated, illnesses such as heat cramping, heat stroke, heat exhaustion, desert syndrome, and heatstroke can occur. In severe cases of dehydration organs do not function properly or may fail.

Thus, it is desirable that an individual's hydration level is monitored regularly and any dehydration is detected in the early stages before an individual's performance levels are impacted or they reach a serious dehydration condition. However, people are often not aware of dehydration symptoms at early stages, based only on self-awareness. As a result, dehydration symptoms are left untreated until an individual feels dizzy or weak and thus realizes something is wrong. By the time an individual feels dizzy or weak they are already in a serious dehydration condition. When an individual reaches a serious dehydration condition, serious medical treatment may be required and the window to treat the individual may become severely shortened.

SUMMARY

This summary is provided to introduce a selection of concepts in a simplified form that are further described below in the Detailed Description. This summary is not intended to identify key factors or essential features of the claimed individual matter, nor is it intended to be used to limit the scope of the claimed individual matter.

There are various ways that have been attempted in detecting the early stages of dehydration that have yielded unsuccessful results. An object of the present invention is to provide hydration information about an individual by monitoring an individual's internal bodily measurements, biometric, biological, and/or physiological state. The hydration condition of an individual also may be affected by their surrounding environment and by monitoring the external surroundings of an individual and/or the environmental conditions approximate an individual, wherein appropriate corrections and normalizations to the biological data may be performed. The individual's biometric, biological, and/or physiological state may be monitored in real-time by using one or a plurality of sensors. The information, data, or measurements taken by one or a plurality of sensors may be analyzed separately or in combination, such as a multimodal analysis or multivariate analysis, to determine an individual's hydration level or dehydration state as well as other important and useful parameters such as body temperature, hematocrit, electrolyte concentrations and so on.

DETAILED DESCRIPTION

Figure 1:
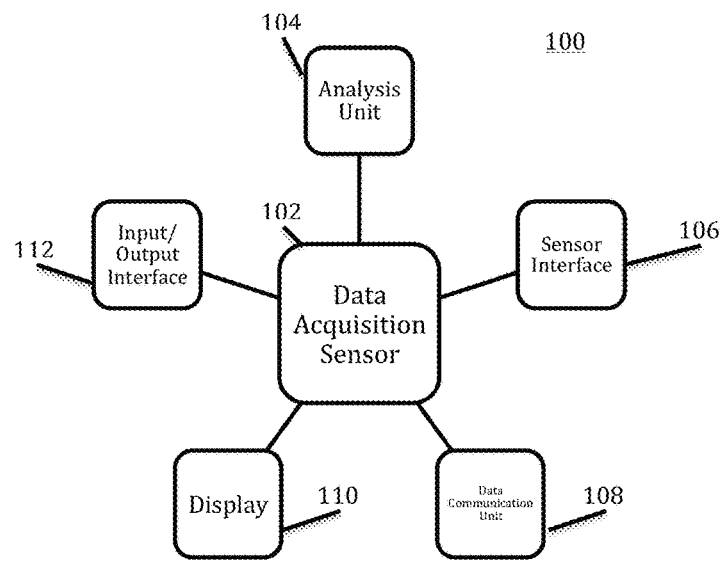
FIG. 1 is a block diagram of a hydration monitoring apparatus according to one embodiment of the present invention.

In one embodiment of the invention, a hydration monitoring apparatus 100 for monitoring an individual's hydration information comprises: a data acquisition unit 102, an analysis unit 104, a sensor interface 106, a data communication unit 108, a display 110, and a input/output interface 112. In another embodiment of the invention, the invention may be a device, system, method, or process.

The claimed individual matter is now described with reference to the drawings, wherein like reference numerals are used to refer to like elements throughout. In the following description, for purposes of explanation, numerous specific details are set forth in order to provide a thorough understanding of the claimed individual matter. It may be evident, however, that the claimed individual matter may be practiced without these specific details. In other instances, well-known structures and devices are shown in block diagram form in order to facilitate describing the claimed individual matter.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

FIG. 1 shows the components of the hydration monitoring apparatus 100 according to an embodiment of the present invention. FIG. 1 shows that the hydration monitoring apparatus 100 may comprise at least one of a data acquisition unit 102, analysis unit 104, sensor interface 106, data communication unit 108, a display 110, and an input/output interface 112.

The data acquisition unit 102 is connectable or in communication and receives and/or sends data to at least one of the analysis unit, sensor interface 106, data communication unit 108, input/output interface 112, and the display 110 connected to or in communication with it. The data acquisition unit 102 may be used to gather, store, record, and/or arrange data collected by the sensor interface 106 and/or analysis unit 104.

Components of the hydration monitoring apparatus 100 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of the hydration monitoring apparatus 100 may be interconnected by a network.

The hydration monitoring apparatus 100 may comprise a sensor interface 106 that has at least one sensor, monitor, or apparatus connected to it for data collection. The sensor interface 106 is in communication with the data acquisition unit 102.

The hydration monitoring apparatus 100 may comprise a data communication unit 108 that can send and receive information between the data acquisition unit 102 and external devices. In one embodiment of the invention, the data communication unit 108 comprises a transceiver. Alternatively, the data communication unit 108 may send and receive data collected by the hydration monitoring apparatus to an external device via a wireless connection or a wired connection. The wireless connection of the data communication unit 108 may transmit the data via such communications systems or connections including a wireless network, Bluetooth, Zigbee, cellular network, and/or other communication systems or devices. The wired connection of the data communication unit 108 may transmit the data via such communications systems or connections including a USB interface, Ethernet connection, a headphone jack, and/or other communication systems or devices. In another embodiment the data communications unit may store the collected data on a non-transitory computer readable medium such as a Compact Disc (CD), Digital Video Disc (DVD), hard drive, or USB storage device, and/or other non-transitory computer readable mediums.

In one embodiment of the invention, the data communication unit 108 may also comprise communication connection(s) that allows the hydration monitoring apparatus 100 to communicate with other devices. Communication connection(s) may include, but is not limited to, a modem, a Network Interface Card (NIC), an integrated network interface, a radio frequency transmitter/receiver, an infrared port, a USB connection, or other interfaces for connecting the hydration monitoring apparatus 100 to other computing devices. The data communication unit 108 may transmit and/or receive communication media.

The hydration monitoring apparatus 100 may comprise an input/output interface 112 in communication with the data acquisition unit 102. The input/output interface 112 may allow for the exchange of information and/or data with external devices, systems, and/or apparatuses. The input device(s) may include devices such as a keyboard, mouse, pen, voice input device, touch input device, infrared cameras, video input devices, and/or any other input device. The output device(s) may include device(s) such as a display, speaker, printer, and/or any other output device(s). In one embodiment, an input device or an output device from another computing device may be used as an input device(s) or an output device(s) for the input/output interface 112.

The hydration monitoring apparatus 100 may comprise a display 110 for presenting information communicated from the data acquisition unit 102 to an individual. The display 110 may comprise a computer, cellular phone, touch screen, short message service (SMS), or other display devices. In one embodiment of the invention, the output device comprises an informing device or display that sends an indication message, which informs or alerts the individual of their body water level, hydration level, dehydration condition, or that the individual is dehydrated or is approaching dehydration.

Figure 2:
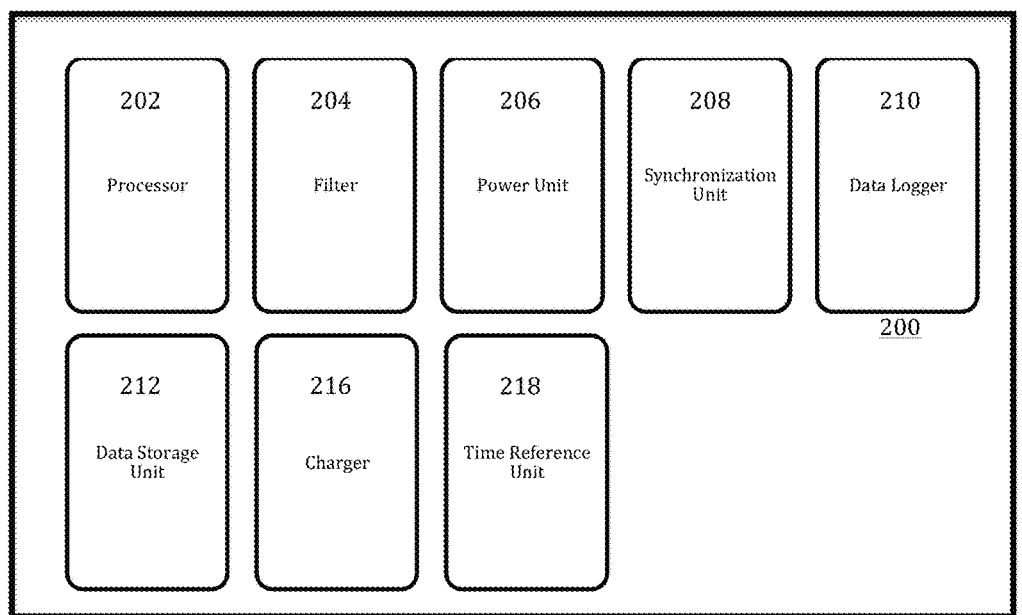
FIG. 2 is a block diagram of a data acquisition unit according to one embodiment of the present invention.

In one embodiment of the invention, input/output interface 112 may include a variety of features and/or functionality. For example, Input/output interface 112 may include additional storage (e.g., removable and/or non-removable) including, but not limited to, magnetic storage, optical storage, and the like. In one embodiment of the invention, computer readable instructions to implement one or more embodiments provided herein may be in storage on a non-tangible computer readable medium in the data communication unit 108 or data acquisition unit 102. FIG. 2 shows one embodiment of a data storage unit 212. The data storage unit 212 or data logger 210 of the data acquisition unit 200 may also store other computer readable instructions to implement an operating system, an application program, and the like. Computer readable instructions may be loaded in memory for execution by processor 202 of the data acquisition unit 200.

In one embodiment of the invention, a sensor interface 106 supplies an alternating current to at least one connected sensor and/or contact point of the at least one sensor. Alternatively the sensor interface 106 may comprise an oscillator. The sensor interface 106 may be arranged to receive synchronization signals, adjust the frequency of the oscillator, and/or adjust the times at which data is collected using an attached sensor(s) and/or contact point(s) of the sensor(s). The synchronization signals may also be used to synchronize the times at which data or information is collected from a plurality of attached sensors.

The term "non-transitory computer readable medium" as used herein includes computer storage media. Non-transitory computer readable media includes volatile and non-volatile, removable and non-removable media implemented in any method or technology for storage of information such as computer readable instructions or other data. The data storage unit 212 is an example of a non-transitory computer readable media. Non-transitory computer readable media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by the data acquisition unit 102. Any such non-transitory computer readable media may be part of the hydration monitoring apparatus 100.

Those skilled in the art will realize that storage devices utilized to store computer readable instructions may be distributed across a network. For example, a computing device accessible via a network may store computer readable instructions to implement one or more embodiments provided herein. The hydration monitoring apparatus 100 may access computing device(s) and download a part or all of the computer readable instructions for execution. Alternatively, the computing device(s) may download pieces of the computer readable instructions, as needed, or some instructions may be executed at computing device(s) and some at hydration monitoring apparatus 100.

In one embodiment the computing device(s) include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

In one embodiment, the data acquisition unit 102 and/or the hydration monitoring apparatus 100 includes at least one processor, such as processor 202, and/or memory. The memory may be volatile (such as RAM, for example), non-volatile (such as ROM, flash memory, etc., for example) or some combination of the two.

FIG. 2 further shows one embodiment of the data acquisition unit 200. The data acquisition unit 200 may comprise a processor 202, filter unit 204, power unit 206, synchronization unit 208, a data logger 210, data storage unit 212, a charger 216, and a time referencing unit 218.

In one embodiment of the invention, the processor 202 may comprise a central processor to process the data and/or information of the other components that comprise the data acquisition unit 200 or the units, interfaces, and/or devices attached to or in communication with the data acquisition unit 200.

In one embodiment of the invention, the filter unit 204 of the data acquisition unit 200 may be used to filter the data received from the units and interfaces in communication unit. The filter unit 204 may filter, categorize, modify, or clean received information and/or data, such as data received or transmitted to and from the sensor interface 106, the data communications unit 108, and the input/output interface 112.

In one embodiment of the invention, the data acquisition unit 200 contains a power unit 206 that supplies power to the data acquisition unit 200 and/or the components of the hydration monitoring apparatus 100. The power unit 206 may comprise a battery to supply power and a charging unit that charges the battery. Alternatively, data acquisition unit 200 and/or the hydration monitoring apparatus 100 are connectable to an energy source that powers the hydration monitoring apparatus 100. In one embodiment of the invention, the charger 216 may be used to recharge a battery or other energy source of the power unit 206.

In one embodiment of the invention, the synchronization unit 208 of the data acquisition unit 200 may be used to synchronize the data and information received and transmitted between the data acquisition unit 200 and the connected devices, interfaces, and units.

In one embodiment of the invention, the data acquisition unit 200 may comprise a data logger 210, wherein the data logger 210 tracks, records, and stores data collected by the data acquisition unit 200 using a non-transitory computer readable medium.

In one embodiment of the invention, the data acquisition unit 200 comprises a time referencing unit 218 that generates time reference data usable to control the time at which data is collected from the sensor interface 106. The time referencing unit 218 may also be used to calculate spatial and/or temporal derivatives between information received from the sensor interface 106. In one embodiment of the invention, the time referencing unit 218 may keep track of the calendar time, such as a clock. Alternatively, the time referencing unit 218 may act as a timer, keeping track of a lapsed time or decrementing from a defined time to zero. The timer of the time referencing unit 218 may be used to collect information or data from the sensor interface 106 for a defined period of time or to record how long the sensor interface 106 collects data.

In one embodiment of the invention, the data acquisition unit 200 receives and/or stores at least one executable program in a data storage unit 212 for execution on a processor 202 of the data acquisition unit 200.

Figure 3:
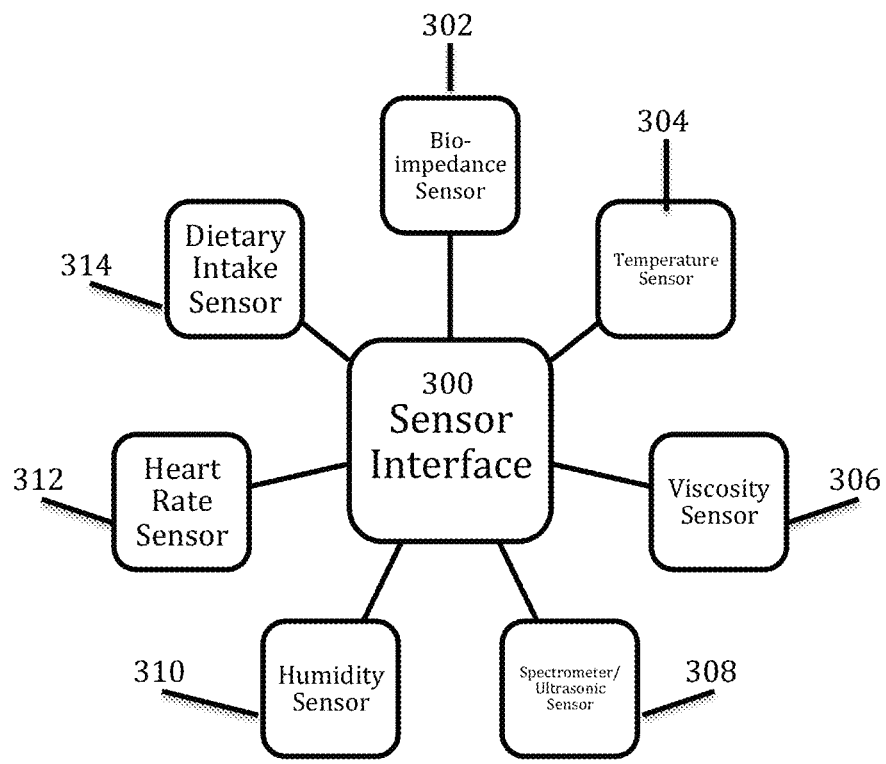
FIG. 3 illustrates a sensor interface and a plurality of sensors, interfaces, and displays that are in communication with the sensor interface.

FIG. 3 shows a plurality of sensors that may be attached or in communication with the sensor interface 300. The sensor interface 300 has at least one sensor attached or in communication with it for data and/or information collection and/or biometric, biological, and/or physiological measurement collection. The attached sensors include at least one of: an impedance sensor 302, a temperature sensor 304, a viscosity sensor 306, a spectrometer or ultrasonic sensor 308, a humidity sensor 310, a heart rate sensor 312, and a dietary intake sensor 314. The sensor interface 300 may alternatively or in addition include: an activity sensor, a communication interface, a data input/output interface, a sodium level sensor, and/or a fluid intake sensor.

The sensors may be attached to the sensor interface 300 using a wireless or wired communication system. In one embodiment of the invention, the at least one sensor comprises at least one contact point that is attached or otherwise connected to an individual. The at least one sensor or contact point of the sensor is attached, embedded, implanted, or otherwise connected to or in contact with an individual. In one embodiment of the invention, one or more of the sensors or contact points of the sensors are mounted or adhering sensors or contact points that are attached to the skin or body of an individual. Alternatively, the sensors or contact points may be embedded in a device or apparatus that is mounted, adheres to, and/or attaches to an individual's body, clothing, or other wearable material. In one embodiment of the invention, the number of contact points and/or the spacing of the contact points of a sensor may vary to enable the sensor(s) or the sensor interface 300 to take measurements and/or monitor along the skin surface of an individual and/or at varying or defined depths of an individual's tissue, interstitial tissue, blood, organs, muscles, vascular system, circulatory system, or other compartments, systems, and/or parts of the individual's body. As the hydration level of an individual changes, the water, interstitial fluid, or other bodily fluid of various parts, compartments, areas, or systems of an individual changes or varies. In one embodiment of the invention, the number of contact points and/or the spacing of the contact points of a sensor may vary to enable the sensors or the sensor interface 300 to take measurements and/or monitor the transfer, pulling, pushing, or movement of water, interstitial fluid, or other bodily fluid from one part, compartment, area, or system of an individual to another part, compartment, area, or system.

In contrast to an individual suffering from dehydration is an individual suffering from a condition such as overhydration, dilutional hyponatremia, hyponatremia, water poisoning, water excess in the body, and/or water intoxication. Such conditions arise from the body containing too much water. At excessively high levels, water can be considered a poison to an individual's body. If an individual's body has too high of a water level the individual's body, organs, or other systems cannot handle the water or fluid level, bodily functions such as kidney functions deteriorate or stop. Too high of water levels in an individual can also cause the body to lack or be unable to retain and/or absorb the proper nutrients it needs to be healthy. In one embodiment of the invention, the sensor(s), contact point(s) of the sensor(s), or sensor interface 300 may detect and the analysis unit 104 determine if an individual's water or fluid levels are increasing, excessive, too high, changing at too quick or too slow of a rate, or otherwise abnormal. The analysis unit 104 may also determine if the hydration level or condition of an individual is dehydrated, low, normal, high, excessive, or overhydrated.

The sensor interface 300, the sensor(s) attached to the sensor interface 300, and/or contact point(s) of the sensor(s) may collect the data in real-time, at defined points or periods of time, at random intervals, or at one point in time. In one embodiment of the invention, the sensor interface 300, the at least one sensor attached to the sensor interface 300, and/or contact point(s) of the sensor(s) may measure an absolute value, relative value, or a rate of change of the information and/or data of biometric, biological, and/or physiological measurements taken. In one embodiment the sensor interface 300, the at least one sensor attached to the sensor interface 300, and/or contact point(s) of the sensor(s) may detect and/or monitor at least one of an individual's: hematocrit, electrolyte level, hydration level, sodium level, and sweat level.

In one embodiment of the invention, the sensor interface 300 or analysis unit 104 may collect, record, store, and/or analyze trends in the data over short periods of time such as seconds, minutes, or hours, and/or extended periods of time, such as days, weeks, months, or years. The collected trend data may be from one or a plurality of the sensors or contact points of the sensors of the sensor interface 300. The analysis unit 104 may use the collected trend data to determine the average rate of change for an individual, group of people, or defined category of people. The group of people may include groups such as families, friends, test groups, selected people with similar traits, or other defined groups. The defined category of people may include categories such as gender, race, ethnicity, age, weight, health condition, diseases, or other defined categories.

In one embodiment of the invention, the analysis unit 104 uses information and/or data from a plurality of sensors to analyze the hydration level of an individual. In one embodiment of the invention, the information and/or data from each of the plurality of sensors may be analyzed separately and/or independently by the analysis unit 104 to determine the hydration level of an individual. Alternatively, the information and/or data from each of the plurality of sensors may be analyzed in combination by the analysis unit 104 to determine the hydration level of an individual. Alternatively, the information and/or data from each of the plurality of sensors may be aggregated, combined, superimposed, or totaled together by the analysis unit 104 to determine the hydration level of an individual. Alternatively, the information and/or data from each of the plurality of sensors may initially be analyzed independently and then the information is aggregated together and analyzed by the analysis unit 104 to determine the hydration level of an individual. Alternatively, the information and/or data from each of the plurality of sensors may initially be aggregated together and analyzed and then the information be analyzed independently by the analysis unit 104 to determine the hydration level of an individual.

In one embodiment of the invention, the analysis unit takes a composite of all the information collected from the at least one sensor to determine the hydration level of an individual. By using the composite information or data in totality the analysis unit may be able to adjust the hydration analysis for incorrect, erroneous, or incomplete measurements. For example, an individual's biological measurements may show or reflect that an individual is becoming dehydrated but a change in the environmental surrounding such as a change in temperature or humidity causes the change in the biological measurements to incorrectly depict the hydration level of an individual. Alternatively, a multi-modal or multivariate analysis or composite analysis is used in determining an individual's hydration level, where a biological measurement such as an impedance measurement taken at one location, depth, part, compartment, and/or system of the body may individually indicate an incorrect or inaccurate hydration level but when taken in combination with other data or information taken from another sensor(s) shows a correct or accurate hydration level of an individual. Accordingly, one advantage of the analysis unit 104 using a combination data or information from the sensors and/or taking the data or information from the sensors in totality is that false reading, inaccuracies, or errors that would arise from analyzing data or information from sensors separately or independently. Another advantage of the analysis unit 104 using a combination data or information from the sensors and/or taking the data or information from the sensors in totality is that the analysis unit may account for changes in the external surroundings or environment of an individual and how such changes might affect the other data or information collected from the sensor(s) or contact point(s) of the sensor(s).

In one embodiment of the invention, the analysis unit 104 and/or the sensor interface 300 uses the combination or composite of the data from the sensor(s) or contact point(s) of the sensor to account and/or adjust for any cross-interference from fluid in different compartments, systems, part, or areas of the body or the transfer and/or movement of the fluid between different compartments, systems, part, or areas of the body. In one embodiment of the invention, the analysis unit 104 and/or the sensor interface 300 uses the combination or composite of the data from the sensor(s) or contact point(s) of the sensor to account and/or adjust for any cross-interference between a plurality of sensors.

In one embodiment of the invention, the analysis unit 104 and/or the sensor interface 300 uses regression analysis, partial least square fitting, filtering, and/or multi-variate analysis in analyzing the data or information collected from the sensor(s). The regression analysis, partial least square (PLS), filtering, and/or multi-variate analysis may be used for one data or information set of one sensor or a plurality of sensors, a plurality of data or information sets of one sensor or a plurality of sensors, and/or the totality of the data or information set from one or a plurality of sensors. The analysis unit 104 and/or the sensor interface 300 may assign the same weighs or importance to the data or information collected from each sensor or contact point of a sensor. Alternatively, the analysis unit 104 and/or the sensor interface 300 may assign different or varying weighs or importance to the data or information collected from each sensor or contact point of a sensor. For example, the analysis unit 104 and/or the sensor interface 300 may give the information or data from an impedance sensor weight of seventy and the give the information or data from a temperature sensor weight of thirty from a total of one hundred in when performing an analysis on the data or information collected from the sensor(s). Alternatively, the analysis unit 104 and/or the sensor interface 300 may disregard, negate, or subtract out the data or information collected from one or more of the sensors or contact points of the sensors in performing the analysis. For example, if a the data collected from a sensor is outside the normal, defined, or overage range for an user, group of individuals, or category of individuals, then the data will be disregarded as erroneous and not included the analysis of the data. The weighting of the data may also assume a dynamic form, where weighting factors are continuously adjusted on history, trends, or user input.

Alternatively, the sensor interface 300 or analysis unit 104 may use the collected data or trends in the data to filter or perform regression analysis on the collected data. The sensor interface 300 or analysis unit 104 may compare the collected data or trends in the data to the current measurements taken by the sensors and/or the recorded change in the data to analyze any atypical or unusual changes in the measurements. Such atypical or unusual changes in the measurements may indicate an error in data collection by the sensor(s), contact point(s) of the sensor(s), and/or sensor interface 300. Alternatively, such atypical or unusual changes in the measurements may indicate a change in the hydration state of an individual, activity level of an individual, or routine of an individual.

Any of the sensors may use bio-impedance, spectroscopy, and/or an optical device to make measurements. In one embodiment of the invention, bio-impedance may be measured by running an electrical current between a plurality of contact points of a sensor. Any of the sensors of the sensor interface 106 may measure the absolute, relative and/or change of absolute or relative level or value of a biometric, biological, and/or physiological signal or indicator of an individual. The analysis unit evaluates the measured change in the absolute or relative sensor values and bases a dehydration analysis at least in part on the change of the absolute or relative sensor values. Alternatively, the sensor interface 300 or the analysis unit 104 may analyze the variance or change of the present or real-time sensors, contact point(s) of the sensors, and/or sensing or measuring apparatus measurements or values with previously collected measurements or values that are stored in a non-transitory computer readable memory of the hydration monitoring apparatus 100.

In one embodiment of the invention, the analysis unit 104 evaluates the data or information from the sensor(s) or contact point(s) of the sensor(s) and determines the level of hydration of an individual. In another embodiment of the invention, the analysis unit 104 evaluates and/or accounts for the rebounding effect of drinking fluid or otherwise hydrating during a monitored period. If an individual drinks during a period of monitoring, such as drinking a sports drink during a workout session or eating soup when sick, there may be a rebounding period where the water level, sweat level, sodium level, electrolyte level, or other levels of the an individual will increase, decrease, or otherwise change. The sensor(s), contact point(s) of the sensor(s), and/or sensor interface 200 may detect such rehydration or rebounding effect and the sensor(s), contact point(s) of the sensor(s), sensor interface 300, and/or analysis unit 104 may take the rehydration or rebounding effect into account in determining the various bodily level(s) of an individual.

In one embodiment of the invention, the sensor interface 300 or data acquisition unit 102 supplies the alternating current at a single frequency. Alternatively, the sensor interface 300 or data acquisition unit 102 supplies a plurality of currents at defined frequencies to the individual. In another embodiment of the invention, the sensor interface 300 or data acquisition unit 102 supplies an alternating current across a frequency spectrum or frequency range.

In one embodiment of the invention, an impedance sensor 302 is connected to the sensor interface 300 and is attached to the individual's body. The impedance sensor 302 can be used to measure the overall amount or the change in the overall amount of fluid, water, sweat, electrolytes, or sodium contained by an individual's body. Alternatively, the impedance sensor 302 can measure the overall amount or the change in the amount of fluid, water, sweat, electrolytes, or sodium contained within an individual's cells. Alternatively, the impedance sensor 302 can measure the overall amount or change in the amount of fluid, water, sweat, electrolytes, or sodium on the surface of an individual's skin or body. In one embodiment of the invention, the impedance sensor 302 measures the change in the sweat rate of the body of an individual or the rate at which an individual is excreting water, sweat, or sodium from his body or cells. A bio-impedance measurement may also indicate changes in the body and/or skin temperature of an individual. Thus, the monitoring of an individual's impedance levels will indicate the individual's level of hydration and if they are becoming dehydrated. In one embodiment, at least one impedance sensor 302 measures an impedance or bio-impedance value for an individual or measures multiple impedance or bio-impedance values collected from the individual. In one embodiment of the invention, the impedance sensor 302 measures the impedance or bio-impedance of an individual by running an electrical current through the body of an individual or along the body or skin surface of an individual using a plurality of sensors or contact points of the sensors. In one embodiment of the invention, the impedance sensor 302 measures the impedance over a specified or continuous frequency range or spectrum. In one embodiment of the invention, the impedance sensor 302, analysis unit 104, and/or the sensor interface 300 accounts and/or adjusts the data or information variance or change in the impedance sensor data based on the effect of a the change in the electrolyte, sodium, water, bodily fluid, or fat of the body of an individual or on the skin surface of an individual. Alternatively, the impedance sensor 302 measures the impedance or bio-impedance using an optical device, spectrometer 308, or ultrasonic sensor 308.

In one embodiment of the invention, the analysis unit 104 receives the impedance or bio-impedance data collected by the impedance sensor 302 and sensor interface 300 and compares the impedance or bio-impedance values with a predetermined or defined value. Alternatively, the analysis unit 104 may analyze the variance or change or the current or real-time impedance or bio-impedance values with previously collected values that are stored in a non-transitory computer readable memory.

In another embodiment of the invention, a temperature sensor 304 is connected to the sensor interface 300. In one embodiment of the invention, the temperature sensor 304 measures the body temperature of the individual. Alternatively, the temperature sensor 304 measures the skin temperature of an individual. Alternatively, the temperature sensor 304 measures the ambient temperature of the area approximate or surrounding an individual. In one embodiment of the invention, the temperature sensor 304 measures the body and/or skin temperature of an individual using a thermostat, thermal-couple, and/or thermistor that is in contact with the body and/or skin of an individual. In another embodiment of the invention, the temperature sensor 304 measures the ambient temperature of an area approximate an individual using a thermostat. Alternatively, the temperature sensor 304 measures the temperature using an optical device, bio-impedance, thermal imaging, or spectroscopy.

In a further embodiment of the invention, a humidity sensor 310 is connected to the sensor interface 300. The humidity sensor 310 measures the absolute or relative level of humidity of the area approximate an individual for a defined period, point in time, or multiple points in time. Alternatively, the humidity sensor 310 measures the absolute or relative level of humidity approximate an individual over a period of time.

In a further embodiment of the invention, a heart rate sensor 312 is connected to the sensor interface 106. The heart rate sensor 312 measures the number of beats of an individual's heart over a defined period of time, i.e. the heart rate. The heart rate sensor 312 may detect the number of beats of a heart by sensing the electrical signal transmitted by the heart. Alternatively, the heart rate sensor 312 may detect the number of beats of a heart by using an optical device, bio-impedance, or spectroscopy.

In a further embodiment of the invention, a sodium level sensor is connected to the sensor interface 106. The sodium level sensor measures the amount of sodium or salt secreted or excreted by an individual over a period of time. Alternatively, the sodium level sensor may measure the sodium or salt amount contained within the cells of an individual or on the surface of the skin of an individual using an optical device, bio-impedance, or spectroscopy. The sodium level sensor may measure the absolute or relative amount of sodium or salt at a defined time or over a defined period of time.

In a further embodiment of the invention, a viscosity sensor 306 is connected to the sensor interface 300. In one embodiment the viscosity sensor 306 measures the skin viscosity of an individual. Alternatively, the viscosity sensor 306 measures the blood viscosity of an individual. The blood viscosity increases, i.e. the blood becomes thicker, as an individual becomes increasingly dehydrated, and thus the blood flow of an individual decreases. The skin viscosity increases, i.e. the skin becomes less elastic, as an individual becomes increasingly dehydrated. In one embodiment of the invention, the viscosity measuring apparatus may measure the skin or blood viscosity of the individual using an optical device, Doppler sensor, bio-impedance, spectroscopy, or a heart rate sensor.

In a further embodiment of the invention, a dietary intake sensor 314 is connected to the sensor interface 300. In one embodiment of the invention, the dietary intake sensor 314 measures the amount of fluid or food an individual intakes into their body. As an individual's dietary intake level varies, the individual's hydration level may also vary. If an individual's fluid intake increases over a period of time it may increase the period of time before an individual becomes dehydrated or feels the effect of dehydration. Similarly, if an individual's fluid intake decreases over a period of time it may decrease the period of time for the individual to become dehydrated or feel the effects of dehydration. The diet habits of an individual may also affect the hydration level and hydration retention level of an individual. For example, as an individual intakes more sodium or fat the individual's body may retain more fluid or water. The individual's dietary intake may be measured in a variety of ways. In one embodiment, an individual's dietary intake is manually entered by the individual using an interface such as a computer, cellular phone, or keyboard. Alternatively, an individual's dietary intake may be measured automatically with a sensor in a fluid or food container, an optical device, bio-impedance, spectroscopy, or a sensor embedded or implanted within the individual's body such as the mouth.

In a further embodiment of the invention, an activity level sensor is connected to the sensor interface 300. In one embodiment of the invention, the activity level sensor measures the amount of activity an individual engages in over a given period of time. As an individual increases their exertion levels over a period of time, the individual may excrete an increased amount of sweat, water, or fluid and thereby lower their hydration or fluid level. Similarly, if an individual decreases their activity or exertion level over a period of time, the individual may excrete almost zero sweat, water, or fluid or a decreased amount of sweat, water, or fluid and thereby remain hydrated for a longer period of time. The activity level sensor may be measured in a variety of ways. In one embodiment of the invention, the activity level sensor utilizes a gyroscope or pedometer for measure the amount of movement or activity by an individual. Alternatively, the activity level sensor may utilize a GPS unit to monitor the movement, speed, or distance traveled by the individual to measure the individual's activity level. Alternatively, the altitude of an individual or the change in altitude may affect the amount of effort or energy expended in order to perform an activity. In one embodiment of the invention, the activity level sensor may utilize an altimeter to at least partially measure an individual's activity level. Alternatively, the activity level sensor may utilize an optical device, bio-impedance, spectroscopy, or heart rate monitor to measure the individual's activity level.

The sensor interface 300 communicates the measurements taken by one or more attached sensors, contact point(s) of the sensors, and/or sensing or measuring apparatuses attached to the sensor interface 300 to the data acquisition unit 200. The data acquisition unit 200 communicates the measurement data or information collected by the sensors, contact point(s) of the sensors, and/or sensing or measuring apparatuses attached to or in communication with the analysis unit 200. The analysis unit 200 evaluates the one or more measurements from the one or more sensors, contact point(s) of the sensors, and/or sensing or measuring apparatuses and bases a hydration analysis at least in part on the data and information from the one or more sensors and sensing or measuring apparatuses.

Figure 4:
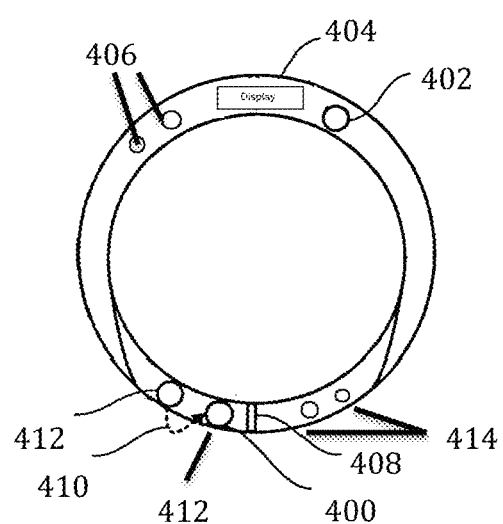
FIG. 4 illustrates a plurality of sensors embedded on the inner radial and outer radial surface of sweatband according to one embodiment of the present invention.

FIG. 4 depicts one embodiment of a sweatband 400 with a sensor or array of sensors that is connected to the sensor interface. In one embodiment the sensor array may be attached or embedded in a device such as a headband, armband, sweatband, chest band, wrist band, leg band. The sensor array may include, but is not limited to, at least one of the following sensors and interfaces: an impedance sensor 302, a temperature sensor 304, a viscosity sensor 306, spectrometer or ultrasonic sensor 308, a humidity sensor 310, a heart rate sensor 312, a dietary intake sensor 314, an activity sensor, a communication interface, a data input/output interface, a sodium level sensor, and/or a fluid intake sensor. The sensor(s) 402 and/or the contact point(s) 406 of the sensors in the sensor interface 300 may be in contact with the surface or otherwise non-invasively in contact with an individual, such as a contact on the skin surface, eyes, fingernails, or hair of the individual. Alternatively, the sensor(s) 402 and/or the contact point(s) 406 of the sensors in the sensor interface may be in invasive contact with an individual. FIG. 4 depicts one embodiment of the invention where the sensor(s) 402 or contact point(s) of the sensor(s) 406 are attached on the interior or inner radius of the device. FIG. 4 also depicts a sensor array where the sensor(s) 412 or contact point(s) of the sensors 414 are attached on the exterior surface or outer radius of the device and are not in contact or noninvasively in contact with an individual. The sensor(s) 402 and 412 or contact point(s) of the sensor(s) 406 and 414 of sensor arrays of FIG. 4 may or may not be in contact with the skin of an individual or may comprise a combination of the sensors with at least one sensor 402 or contact point 406 of the sensors in contact with the skin and at least one sensor 412 or contact point 414 of the sensors not in contact with the skin of the individual. FIG. 4 also depict that the sensor interface 300 may comprise a display device 404 for presenting information or sending an alert to an individual. In one embodiment of the invention, FIG. 4 depicts a plurality of sensors 412 that run an electrical current 410 between the plurality of sensors 412 to take measurements. Alternatively, a plurality of contact points 414 may run an electrical current between the plurality of contact points 414 to take measurements.

Figure 5A:
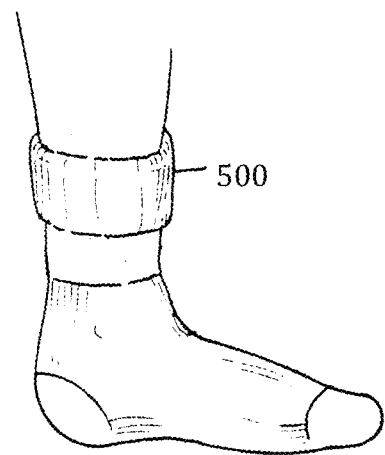
FIGS. 5a, 5b, and 5c illustrate a plurality of positions the sweatband could be located on an individual's body.
Figure 5B:
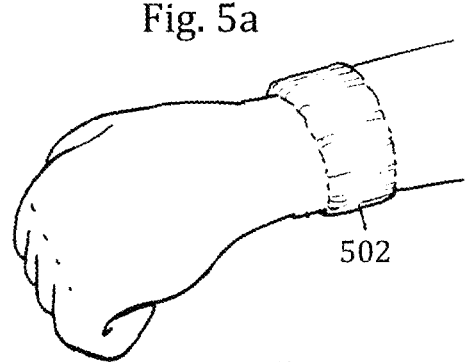
Figure 5C:
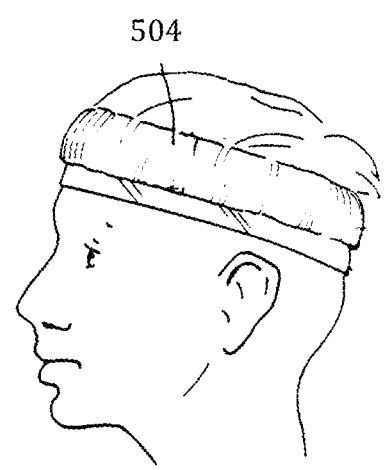

FIGS. 5a, 5b, and 5c depicts a plurality of positions on the individual's body that the sensor interface 300, sensor(s), and/or contact point(s) of the sensors, or the hydration monitoring apparatus 100 may be attached to the individual. The hydration monitoring apparatus 100 may be attached to the individual's head using a headband, to the individual's chest using a chest band, to the individual's arm or wrist using an armband, to the individual's ankle using an ankle band, or otherwise attached to an individual's body using a sweatband, bandage, band, watch, bracelet, ring, adherent, or other attachments and connections. FIG. 5a depicts the hydration monitoring apparatus 100 attached to the foot or ankle 500 of an individual. FIG. 5b depicts the hydration monitoring apparatus 100 attached to the arm or wrist 502 of an individual. FIG. 5c depicts the hydration monitoring apparatus 100 attached to the head 504 of an individual. The sensor interface 300, sensor(s), and/or contact point(s) of the sensors, or the hydration monitoring apparatus 100, and/or sensor array may alternatively be attached to the individual by integrating it into the apparel or garments of the individual or by otherwise attaching it to the individual.

Figure 6:
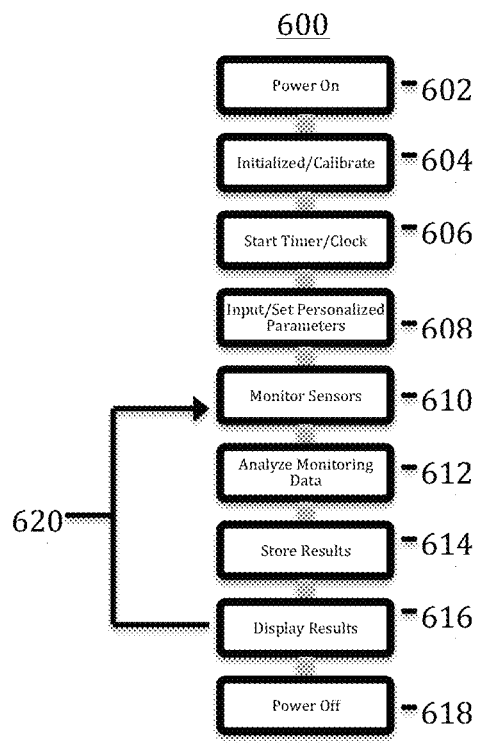
FIG. 6 is a flowchart illustrating the action flow of the hydration monitoring apparatus according to one embodiment of the present invention.

FIG. 6 depicts one embodiment of the process 600 employed by the hydration monitoring apparatus 100. In step 602, the hydration monitoring apparatus 100 is powered on. In step 604, the hydration monitoring apparatus 100 is initialized and/or calibrated. In step 606, a time reference of the time reference unit 218, such as a clock or timer is set. In step 608, the personalized settings of the individual are input and/or set. In step 610, the hydration monitoring apparatus 100 monitors the sensors attached to the sensor interface 106. In step 612, the analysis unit analyzes the data or information received from sensors, units, devices, and/or interfaces in communication with the data acquisition unit 102. In step 614, the data logger 210 of the data acquisition unit 200 stores the acquired data and information. In step 616, the results of the acquired data and information and the analyzed data and information are displayed. In step 618, the hydration monitoring apparatus 100 is powered off.

Figure 7:
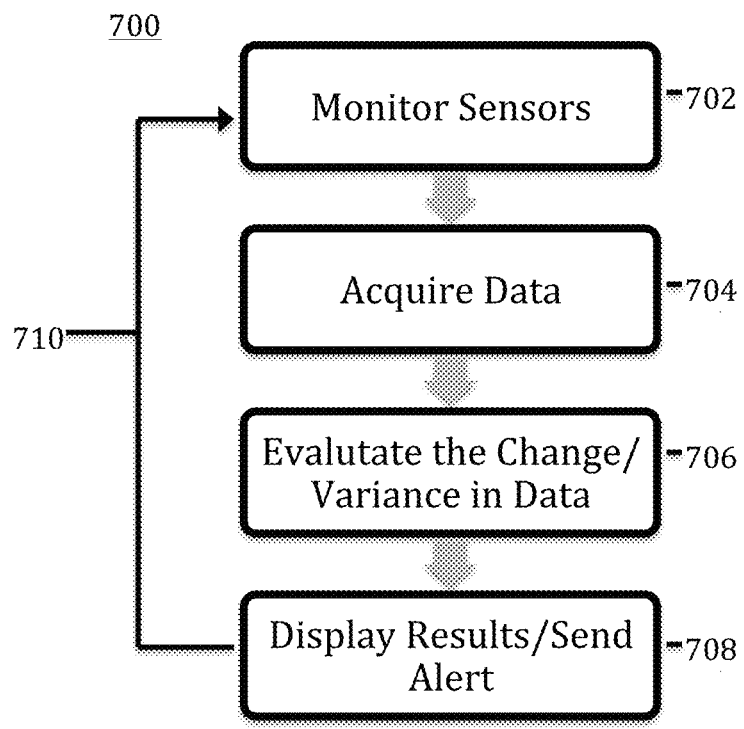
FIG. 7 is a flowchart illustrating the action flow of the monitoring and analysis of an individual for one embodiment of the hydration monitoring apparatus according to the present invention.

FIG. 7 depicts one embodiment of the process 700 employed by the data acquisition unit 102. In step 702, the data acquisition unit 102 monitors the units and interfaces that are in communication with it or attached to it. In step 704, the data acquisition unit 102 acquires data from the sensors or contact point of the sensors of the sensor interface 106. In step 706, the analysis unit evaluates the real time data and information and/or the data and information acquired and/or stored in the data logger 210 of the data acquisition unit 200. In step 706, the analysis unit may also determine if there is a variance or change in the acquired, present, real-time, and/or previously acquired data. In step 708, the hydration monitoring apparatus 100 displays the acquired, present, or real-time data and information and/or the results of the analyzed data. Alternatively, in step 708, the hydration monitoring apparatus 100 may alert the individual or a third party regarding the acquired, present, real-time, and/or previously acquired data and information and/or the results of the analyzed data.

Figure 8A:
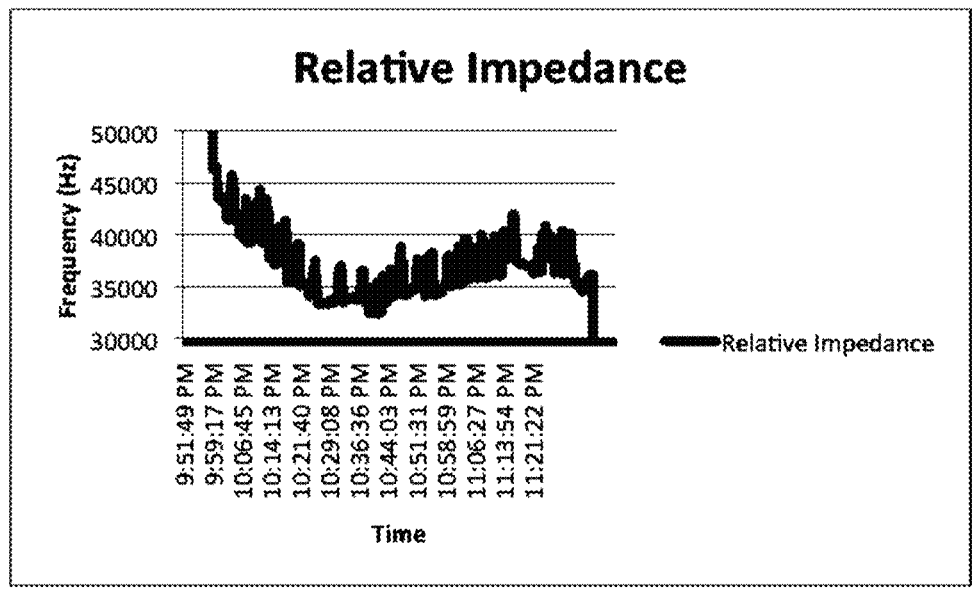
FIG. 8a is a graph illustrating the impedance over time data for a individual that is hydrated.

A typical set of impedance readings is presented in FIG. 8a for a normally hydrated individual that excreting sweat during a period of activity. As the individual begins to sweat the impedance reading begins to decrease. As the individual continues to exert himself over time the individual will increasingly excrete more sweat until they reach a peak rate of sweating. The normally hydrated individual will continue to sweat at that peak rate of sweating until they decrease the level of exertion for the activity or stop the exertion activity.

Figure 8B:
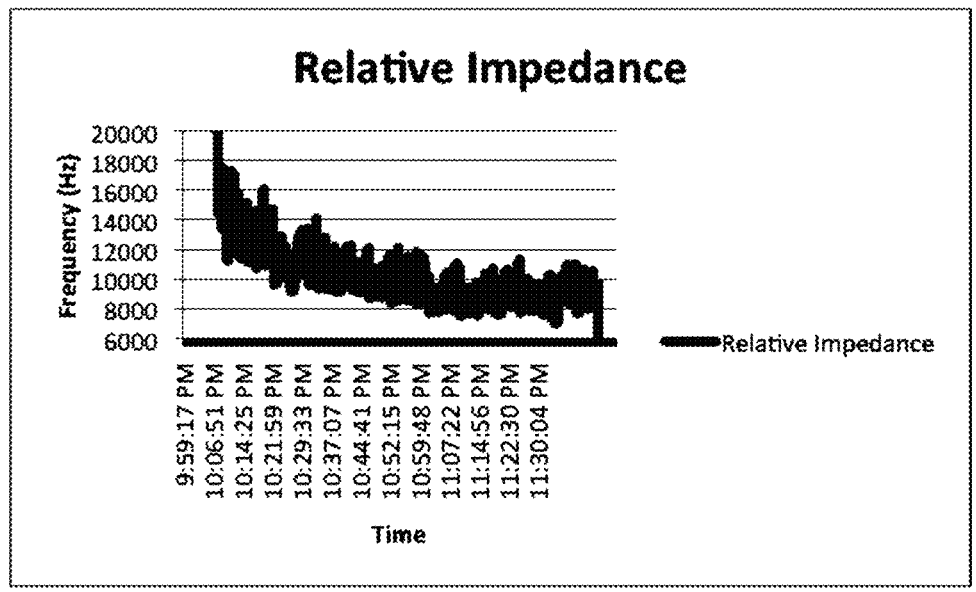
FIG. 8b is a graph illustrating the impedance over time data for a individual that is becoming dehydrated.

A set of bio-impedance readings is presented in FIG. 8b for an individual becoming dehydrated due to excreting sweat during a defined period of activity. As the individual begins to sweat the impedance reading begins to decrease. As the individual continues to exert himself over the defined period of time, the individual will increasingly excrete more sweat until they reach a peak rate of sweating. However, as the individual becomes dehydrated he will continue to exert himself at the same approximate level but will excrete less sweat because the body fluid or sweat level is lowered and his body is unable to continue to excrete sweat at the peak rate of sweat. The dehydrated individual will continue to excrete less sweat as he continues to exert himself during the activity and thus the measured impedance reading will increase in ohms as the individual becomes more dehydrated.

Various operations of embodiments are provided herein. In one embodiment, one or more of the operations described may constitute computer readable instructions stored on one or more non-transitory computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Although the individual matter has been described in language specific to structural features and/or methodological acts, it is to be understood that the individual matter defined in the appended claims is not necessarily limited to the specific features or acts described above. Rather, the specific features and acts described above are disclosed as example forms of implementing the claims.

As used in this application, the terms "device," "unit," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed individual matter may be implemented as a method, apparatus, or article of manufacture using standard programming and/or engineering techniques to produce software, firmware, hardware, or any combination thereof to control a computer to implement the disclosed individual matter.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated exemplary implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. An electronic device comprising:
    a housing;
    a sensor array integrated into the housing, the sensor array comprising:
        an impedance sensor comprising:
            a first contact point configured to send an electrical current at a defined tissue depth for a defined body location to a second contact point; and
            the second contact point configured to receive the electrical current;
        an optical spectrometer is configured to measure light reflection for the defined body location at a frequency range to obtain a light reflection measurements; and
        an environmental sensor configured to take an environmental measurement;
    a processor coupled to the sensor array, wherein the processor is configured to:
        measure, using the sensor array, a first set of impedance measurements and a first set light reflection measurements;
        measure, using the sensor array, a second set of impedance measurements and a second set of light reflection measurements;
        determine a relative change between a first impedance range for the first set of impedance measurements and a second impedance range for the second set of impedance measurements;
        determine a relative change between a first light reflection range for the first set of light reflection measurements and a second light reflection range for the second set of light reflection measurements;
        determine a hydration condition measurement for a body based on the relative change between the first impedance range and the second impedance range and the relative change between the first light reflection range and the second light reflection range, wherein:
            a negative relative change is associated with an increased excretion of fluid that is indicative of dehydration; and
            a positive relative change is associated with a decreased excretion of fluid that is indicative of rehydration or a rebounding effect;
        receive, from the environmental sensor, the environmental measurement; and
        adjust the hydration condition measurement for the body based on the environmental measurement; and
    a display device integrated into the housing, wherein the display device is configured to display a hydration condition indicator associated with the hydration condition measurement, the hydration condition indicator indicating a hydration condition of the body.

2. The electronic device of claim 1, wherein the processor is configured to determine the relative change using a multivariate analysis of the first and second set of impedance measurements, the first and second set of light reflection measurements, and the environmental measurement.

3. The electronic device of claim 1, wherein the processor is configured to determine the relative change using a partial least squaring analysis of the first and second set of impedance measurements, the first and second set of light reflection measurements, and the environmental measurement.

4. The electronic device of claim 1, wherein:
    the sensor array further comprises an additional sensor, wherein the additional sensor is: a temperature sensor, a viscosity sensor, a ultrasonic sensor, a heart rate sensor, a dietary intake sensor, an activity sensor, a sodium level sensor, or a fluid intake sensor; and
    the sensor array is configured to take a biological measurement using the additional sensor.

5. The electronic device of claim 4, wherein the processor is configured to determine the relative change using a multivariate analysis of the first and second set of impedance measurement, the first and second set of light reflection measurement, the environmental measurement, and the biological measurement.

6. An electronic device comprising:
    a housing;
    a sensor interface integrated into the housing, the sensor interface comprising:
        an impedance sensor comprising:
            a first contact point configured to send an electrical current to a second contact point; and
            the second contact point configured to receive the electrical current;
    a processor coupled to the sensor interface, wherein the processor is configured to:
        take a plurality of impedance measurements over a period of time using the impedance sensor;
        receive, from sensor interface, the plurality of impedance measurements;

determine a rate of change for the plurality of impedance measurements over the period of time;

determine a hydration condition measurement for a body based on the rate of change of the plurality of impedances measurements, wherein:

an increased rate of change is associated with an increased excretion of fluid that is indicative of dehydration; and a decreased rate of change is associated with a decreased excretion of fluid that is indicative of rehydration or a rebounding effect; and a display integrated into the housing, wherein the display is configured to display a hydration condition indicator associated with the hydration condition measurement, the hydration condition indicator indicating a hydration condition of the body.

7. The electronic device of claim 6, further comprising a memory coupled to the processor, wherein the memory is configured to store the plurality of impedance measurements taken over the period of time.

8. The electronic device of claim 6, wherein the processor is to determine:

a variance in an impedance level for the plurality of impedance measurements over the period of time; and determine the hydration condition measurement for the body based on the variance in the plurality of impedances measurements, wherein the variance in the plurality of impedances measurements is a relative amount of change of the impedance level over the period of time.

9. The electronic device of claim 6, wherein the processor is configured to:

determine a variance between impedance levels of the plurality of impedance measurements over the period of time; and determine the hydration condition measurement for the body based on the variance between the impedance levels, wherein the variance in the impedance levels is an amount of change of the impedance levels at a point in time.

10. The electronic device of claim 6, wherein the processor is to take the impedance measurements continuously for the period of time when the impedance sensor is adapted to be coupled to the body.

11. The electronic device of claim 10, further comprising a memory coupled to the processor, wherein the memory is configured to store a historical impedance measurement, wherein the rate of change is determined based on change between the historical impedance measurement and the plurality of impedance measurements continuously taken for the period of time.

* * * * *